United States Patent [19]

Cohen et al.

[11] 4,143,648
[45] Mar. 13, 1979

[54] PORTABLE THERAPEUTIC APPARATUS HAVING PATIENT RESPONSIVE FEEDBACK MEANS

[75] Inventors: Ronald S. Cohen; James M. Dawley, both of Milwaukee, Wis.

[73] Assignee: Behavioral Controls, Inc., Milwaukee, Wis.

[21] Appl. No.: 787,064

[22] Filed: Apr. 13, 1977

[51] Int. Cl.² .................. A61B 19/00; G09B 19/04
[52] U.S. Cl. .................... 128/1 R; 179/1 N; 179/1 SC; 35/35 C
[58] Field of Search ............. 128/2.08, 1 C, 2 R, 128/2 N, 2 Z, 2.1 A, 1 R; 73/585; 179/1 AA, 1 AL, 1 SB, 1 SC, 1 SD, 107 R, 1 N; 181/126–127; 35/35C

[56] References Cited

U.S. PATENT DOCUMENTS

| | | | |
|---|---|---|---|
| 3,101,390 | 8/1963 | Maille | 128/1 R |
| 3,281,534 | 10/1966 | Dersch | 179/1 SC |
| 3,316,353 | 4/1967 | Dersch | 179/1 SC |
| 3,368,551 | 2/1968 | Hardyck | 128/2 R |
| 3,566,858 | 3/1971 | Larson | 128/1 R |
| 3,584,618 | 6/1971 | Reinhardt | 128/2.08 |
| 3,645,133 | 2/1972 | Simeth et al. | 128/DIG. 29 |
| 3,677,261 | 7/1972 | Day | 128/DIG. 29 |
| 3,760,108 | 9/1973 | Gacek et al. | 179/1 SC |
| 3,848,091 | 11/1974 | Stearns et al. | 73/585 X |
| 3,949,735 | 4/1976 | Klar et al. | 73/585 X |
| 4,063,550 | 12/1977 | Tiep | 128/2 R |
| 4,064,869 | 12/1977 | DeFares et al. | 128/2 R |

Primary Examiner—Robert W. Michell
Assistant Examiner—Francis J. Jaworski
Attorney, Agent, or Firm—Andrus, Sceales, Starke & Sawall

[57] ABSTRACT

A portable therapeutic instrument includes a microphone to be secured to a patient's throat for monitoring voice level or to a patient's nose for monitoring nasal sounds. An input amplifier includes an automatic gain circuit which essentially flattens the gain curve. An adjustable level detector includes a solid state level detector to generate a square wave signal connected to a logic switching circuit for turning a tone oscillator or other stimulus unit wholly on or off. A second similar channel connected to the input amplifier detects total voiced speech. A switch means connects the oscillator to only the first channel to detect speech above a selected level or to both channels to detect speech only below a selected level. The several channels include time delay circuits permitting normal speech attack and decay. The microphone may also be connected to the patient's nose to monitor nasal sounds.

8 Claims, 6 Drawing Figures

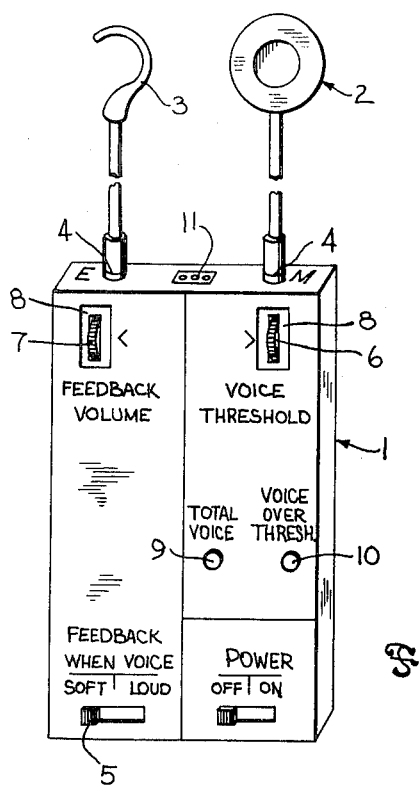
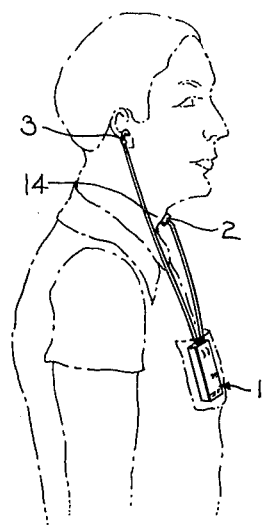
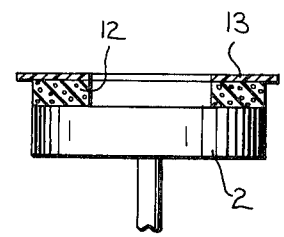
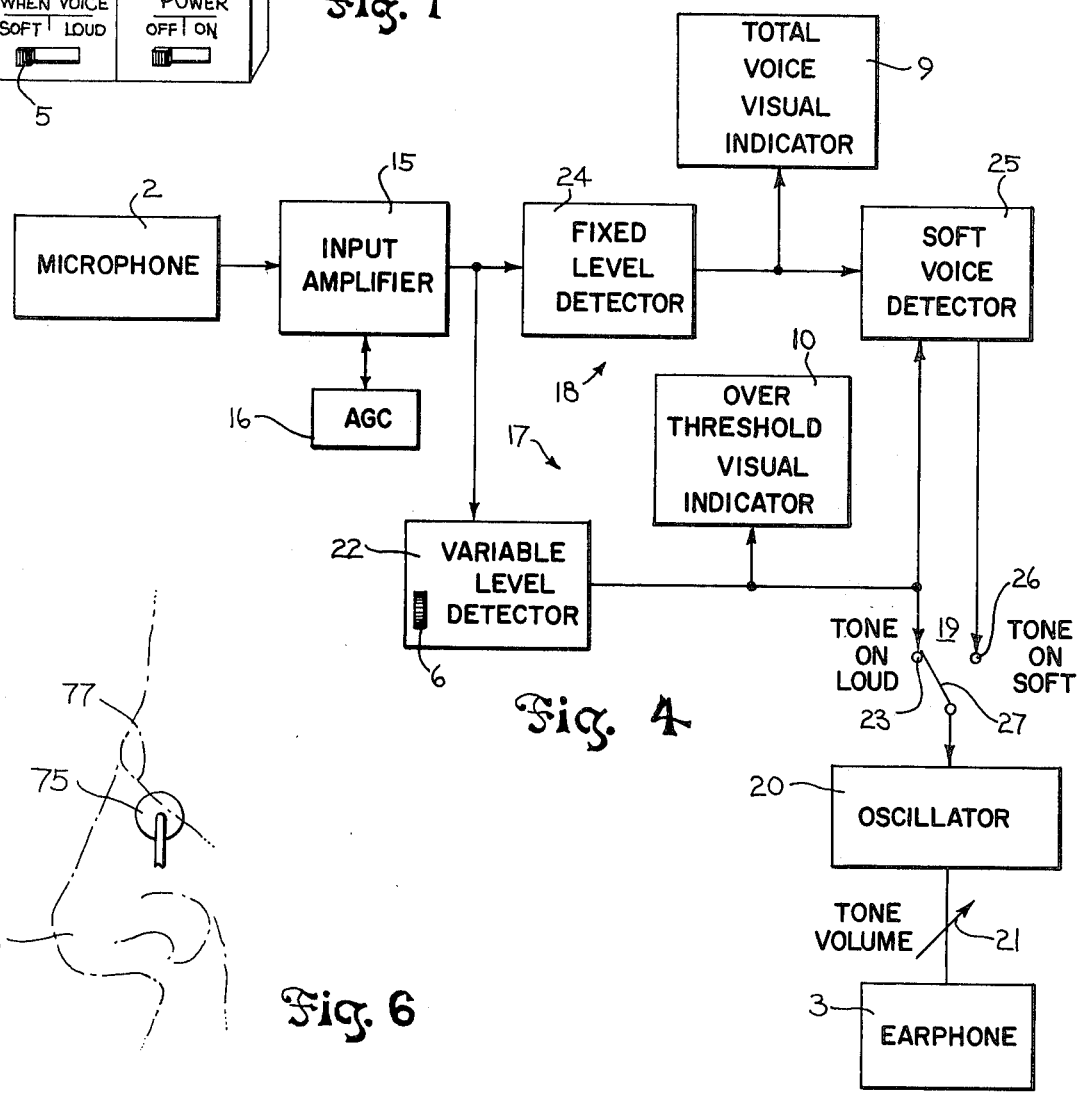
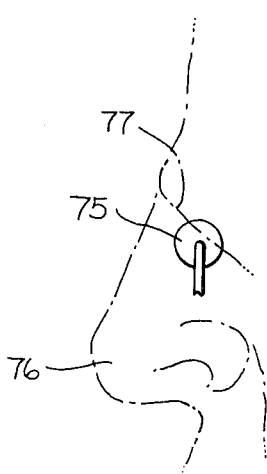

PORTABLE THERAPEUTIC APPARATUS HAVING PATIENT RESPONSIVE FEEDBACK MEANS

BACKGROUND OF THE PRESENT INVENTION

The present invention relates to a therapeutic apparatus having a patient responsive feedback means for monitoring and/or treating the behavior of a patient.

Various human activity involving abnormal or undesirable physical activities and phenomena is preferably instantly detected and disclosed for appropriate treatment. The field of speech and hearing is presently developing behavioral approaches for treating various speech and hearing defects and characteristics to produce controlled modification of verbal behavior. For example, stutterers are often treated using a masking technique in which the subject's voice is masked so he cannot hear himself speak. A portable device has been suggested in which a stutterer is provided with a small throat microphone that actuates a masking sound generator whenever and only while the subject is speaking. The masking sound generator is connected to a pair of ear pieces similar to those utilized in hearing aids which are placed in the subject's ears. The device produces masking therapy while the subject is speaking while allowing unimpeded hearing at other times. A portable auditory feedback device has also been suggested for treating of patients with dysphonia as a result of either vocal cord lesions or laryngeal hypertension. With this device, a small throat microphone is again attached to the patient's throat and an earphone is attached to the patient's ear. The microphone is connected to a sound generator to provide an auditory-feedback signal only in response to predetermined excessive loudness of the speaker's voice. The patient is continuously and instantaneously warned whenever there is an excessive vocal intensity thereby immediately indicating abusive loudness.

The device is fully described in the August, 1974 issue of *The Journal of Speech and Hearing Disorders,* and generally includes suitable sensitivity control for response adjustment in accordance with the particular patient as well as to insure that the tone generator is not activated in the presence of soft, normal breathing patterns. Screwdriver adjustable potentiometers are provided for controlling the sensitivity of the instrument and the feedback loudness of the tone generator. The voice intensity response instrument also included internal timer means providing measurement of total talking time and/or the total loud talking time for monitoring both functions simultaneously. Treatment with such a portable device is highly desirable in that treatment continues while the patients continue to function, including use of their voice. Alternate methods of treatment generally available are complete voice rest for periods up to six weeks or a surgical operation involving vocal cord stripping. Neither of these alternate methods change the habits of the patient and thus the physical ailment or defect may readily reoccur. It also, of course, does not permit continued normal patient functioning during the treatment. Such a device thus provides a significant method of behavioral approach to the modification of verbal behavior of the patient.

The present inventors have found that various response and detection characteristics of the system are highly significant in providing therapy or treatment. In treatment of various vocal disorders the detecting of abnormally low or soft speech may be required as well as excessive loud speech.

SUMMARY OF THE PRESENT INVENTION

The present invention is particularly directed to a patient responsive portable instrument for generating of a feedback signal which is highly responsive to a patient generated activity such as that associated with the patient's speech or the like. In accordance with a significant feature of the present invention the instrument includes dual channels which operate conjointly and with a control selection means to selectively respond to either abnormally loud vocal activity or alternatively abnormally soft vocal activity.

The pair of channels simultaneously detect both lower and upper voice intensity levels, to simultaneously monitor both the total vocal activity and abnormal activity. The sensitivity of the system adapts the device to various types of pick-up including the conventional throat mounted microphone. Other forms, however, which are responsive to other characteristics may also be readily employed. For example, speech with excessive nasal characteristics is a rather common speech problem. With respect to the present invention, the pick-up unit can be readily applied to the nose and provide a biofeedback response related to nasal characteristics. Speech characteristics may also be related to muscle tension. Other physical defects such as headaches and the like may also be related to muscle stress in various head and neck regions. A suitable muscle tension detector may be applied to an appropriate body region to detect any abnormal stress and produce an automatic biofeedback. Similarly, body temperature changes can be detected employing a thermistor. The particular feedback device can readily be any other form than an auditory device and in some applications, other forms are required. For example, a small vibrator might be employed to signal abnormal voice intensity level, muscle stress and the like to the deaf or the deafblind. A small signal lamp could be also provided for the deaf or any other patient having appropriate sight.

More particularly, in accordance with a preferred and particularly unique embodiment of the present invention, the instrument includes a pick-up such as a throat mounted microphone connected to the input of an amplifier which is provided with a sensitive automatic gain control circuit. A particularly satisfactory system employs an opto-isolator for effectively increasing the negative feedback with increasing output to essentially flatten the gain curve. An adjustable level detector includes a solid state level detector to generate a square wave signal which is filtered and inverted to produce a very sharply defined, accurate output signal at a selective input signal level. The output of this variable level detector provides a highly accurate trigger signal which is applied to a triggering circuit such as an inverter for turning on of a suitable tone oscillator. The detector is set to detect signals above a selected level and thereby detect excessively loud voice sounds. The second channel preferably includes a fixed level detector also connected to the output of the input amplifier and provides a channel for detecting total speech time or other physical characteristic being monitored. To monitor abnormally soft level vocal activity, the fixed and adjustable level detector are connected to jointly control the actuation of tone oscillator only at speech below the selected level, such that the oscillator turns positively off as the voice exceeds such level or if the voice is completely stopped. The adjustable level detector holds the tone oscillator off while the fixed level detector turns the oscillator on when the voice drops below the normal level. The circuitry which connects the several channels includes suitable time delay circuitry to permit the normal speech attach and decay which occurs during the normal transitions of speech without triggering the oscillator. Thus, when the patient begins to speak he has sufficient delay before feedback tone onset to allow for normal speed attack, that is for the speech sound to rise above the minimum level. Similarly, transferring from a normal or acceptable speech level to an abnormally low speech level, delay is required to permit normal level of speech decay and also permit stopped consonant intervals. This combination allows the tone oscillator to operate in response to the voice with transition between the three possible conditions of no voice, voice which is too soft, and finally a voice which is loud enough, with the tone occurring only when the voice is too soft for adequate vocal communication.

Accurate detection and rapid switching on and off of the feedback signal combined with proper delay characteristics is highly significant in proper behavioral treatment for speech problems. It is important to prevent unacceptable garbled feedback signals with varying speech characteristics.

The adjustable threshold level and tone level controls are provided with external control devices such as control knobs which are recessed in the housing to prevent unintentional movement of such controls. The patient may then function normally without concern as to the settings. Further, the instrument is designed as a relatively thin compact unit for application to various portions of the body. For adults and responsible patients, the instrument is designed for support on a belt, in a patient's pocket or the like. In connection with children and the like, it may be desirable to strap or otherwise apply the instrument to an inaccessible portion of the patient's body such as the middle of his back.

In addition, in order to permit specialized treatment based on relative durations of the abnormal speech, an outlet accessible through the external wall jacket is connected to the two channels for connection of an external timing device for recording of total phonation time and phonation time above the threshold or a combination thereof. The use of an external timing device is particularly desirable with the development of digital timers which are relatively inexpensive and have the degree of accuracy within the range required for most general clinical and research applications.

The present invention has been found to provide a highly practical, portable biofeedback therapy instrument, particularly adapted to speech therapy.

BRIEF DESCRIPTION OF DRAWINGS

The drawings furnished herewith illustrate a preferred construction of the present invention in which the above advantages and features are clearly disclosed as well as others which can be readily understood from the following description.

In the drawings:

FIG. 1 is a pictorial view of an instrument constructed in accordance with the present invention;

FIG. 2 illustrates the instrument applied to the patient for monitoring vocal abuse;

FIG. 3 is an enlarged view of the microphone shown in FIGS. 1 and 2;

FIG. 4 is a block diagram illustrating a preferred construction of the present invention;

FIG. 6 is a view showing an alternate use of the instrument for monitoring nasal voice speech.

DESCRIPTION OF ILLUSTRATED EMBODIMENT

Figure 5:
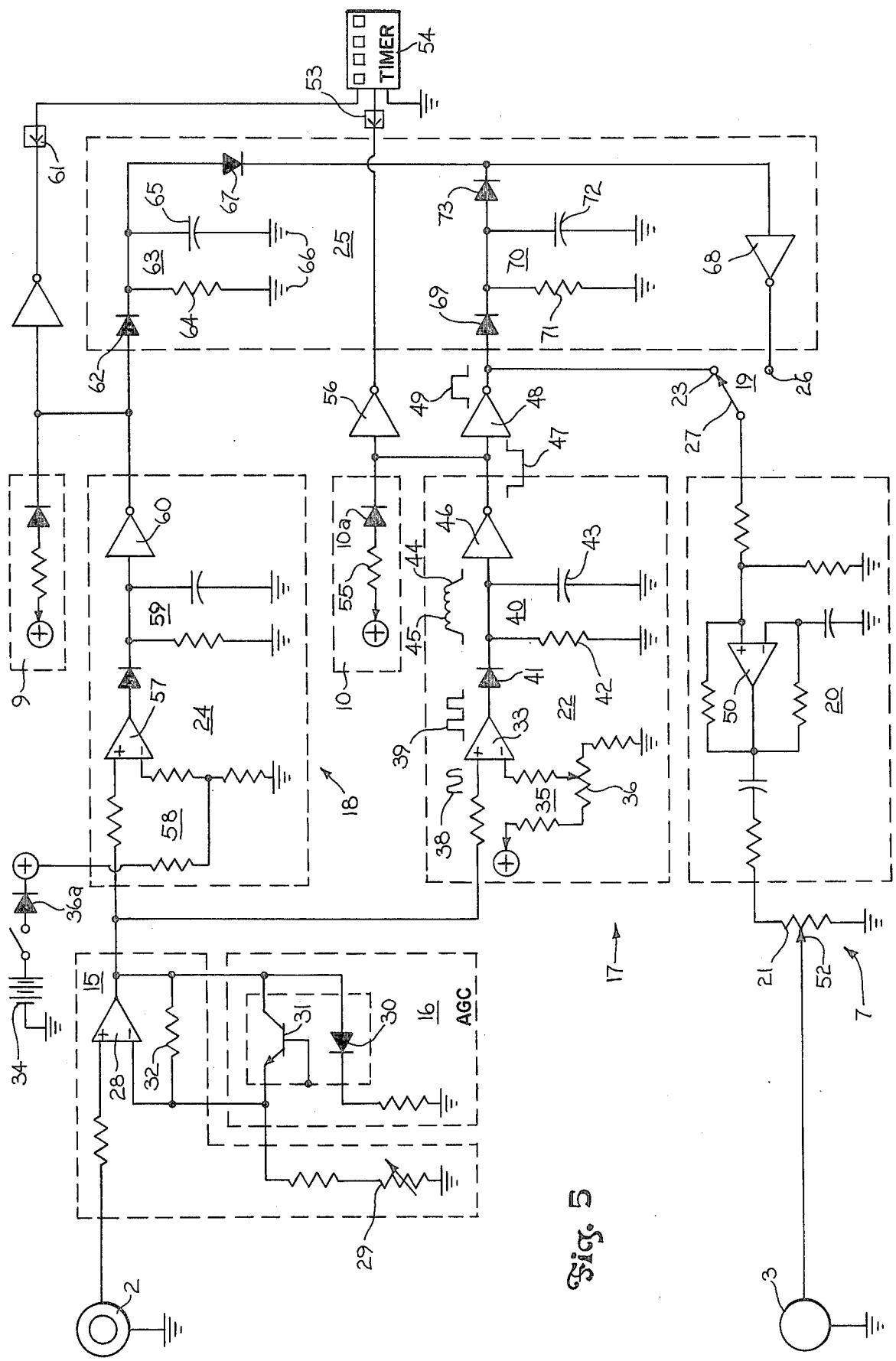
FIG. 5 is a schematic section of the block diagram shown in FIG. 4 and illustrating a preferred construction of the invention.

Referring to the drawings and in particular to FIG. 1, an instrument 1 constructed in accordance with the teaching of the present invention is illustrated. The instrument 1 is formed in a relatively small, compact package or housing which can be readily slipped into a pocket, as shown in FIG. 2, or attached to and carried by a patient by means of a belt clip or commercially available hearing aid harnesses. A small microphone 2 is attached directly to the skin of the patient, generally adjacent to the larnyx, and connected as the instrument input. An earphone is placed in the ear of the patient for automatic signaling of abnormal speech which is either excessively loud or excessively soft. The instrument 1 is provided with jacks 4 on one end for selective and releasable interconnection of the leads of earphone 3 and microphone 2. A control switch unit 5 permits the user to select response to either the abnormally loud or soft sounds but not both. In order to establish accurate response and at different abnormal voice levels for different patients, a variable threshold level control unit 6, shown as a rotating knob, is provided for setting the responses to a particular signal level. Additionally, to further adapt the instrument to particular individuals, a feedback sound level control 7, also shown as a rotating knob is also provided to regulate the intensity of the feedback warning sound signal for adjustment to a comfortable level. The control knobs 6 and 7 are recessed within the housing as at 8, to prevent accidental and unauthorized movement. Individual indicators 9 and 10 such as small LED lamps may be mounted in the case of the control unit to respectively provide a visual indication of voice response and separately of abnormal voice activity. In addition, a three terminal output jack 11 is shown between jacks 4, at which output signals related to the total voice time and abnormal or over threshold voice level time are formed. This permits monitoring of the corresponding voice periods through the releasable interconnection of a suitable external timer, as shown in FIG. 5. Such a timer will normally only be employed during clinical and research applications.

The microphone 2 may be of any suitable construction, such as the known small diaphragm actuated microphone shown in FIG. 3. A soft rubber spacer ring 12 is secured to an outer surface to define a spacing of the diaphragm. A double-faced tape 13 is secured to the outer surface of ring 12 and employed to attach the microphone directly to the skin, preferably immediately on the front of the throat section and particularly immediately below the larnyx 14. The microphone 2 is thus sealed to the skin and generates a signal only when the patient speaks. Referring particularly to the FIG. 4, the block diagram of the instrument in a preferred construction, is illustrated.

The output of the microphone 2 is an electrical signal which is applied directly to the input of an amplifier 15 having an interconnected automatic gain circuit (AGC) 16. The output of the amplifier 15 is connected to a first and second signal processing channel 17 and 18, the outputs of which are selectively connected by a control switch 19 coupled to operator 5. The output of channels 17 and 18 actuate a tone generator 20, shown as an oscillator. The output of the oscillator 20 is connected to a variable level control 21 coupled to control knob 7, the output of which is connected to earphone 3.

The first channel 17 includes a variable level detector 22 adapted to respond to sound peaks of predetermined minimum level as set by the threshold control knob 6. The output of the variable level detector 22 is connected to a suitable visual indicator 10 and to the loud-voice contact 23 of the selection switch 19, shown as a single pole, double throw switch. The second channel 18 includes a level detector 24 which may be fixed, or adjustabled, to respond to essentially any voiced sound generated by the patient. Its output is connected to a total voice visual indicator 9 and to a special soft voice circuit 25, the output of which is connected to the soft sound contact of the sound selection switch 19. The soft voice section 25 has a second input connected to the variable level detector 22. The channels 17 and 18 thus jointly control the tone generator 20 when detecting the soft level characteristic of speech. The section 25 thus functions as a logic circuit means to compare the relative presence and level of speech and provide a feedback signal only on a soft voice condition and following suitable time delays to allow for normal speech transitions.

The selection switch 19 is shown as a single pole double throw switch having a loud voice contact 23 connected to the output of the variable level detector 22 and a soft voice contact 26 connected to the soft voice circuit. A common pole 27 is connected to the tone generator 20. The instrument 1 is set to respond to either abnormally loud sounds or alternatively to abnormally soft sounds. The dual channel system not only permits the selection of the voice characteristic, but also permits the monitoring of the total voice characteristic including abnormally high or soft voice characteristics.

Although the block diagram system can be implemented using any suitable circuitry, FIG. 5 illustrates preferred integrated circuits which provide sensitive and accurate detection and result in a circuit construction which is made compact and readily formed as a portable unit.

Referring particularly to FIG. 5, the amplifier 15 is illustrated as an operational amplifier 28 having a resistor feedback system including a maximum gain control potentiometer 29. The AGC circuit 16 is connected in the feedback circuit, and in the illustrated embodiment of the invention, is shown as a suitable opto-isolator circuit including an LED unit 30 connected to the output of the amplifier 28. The LED unit 30 drives a photo-transistor 31 connected in parallel with a feedback resistor 32 of the operational amplifier 28. Thus, as the output level of the operational amplifier 28 increases, the lamp unit 30 is illuminated and drives the photo-transistor 31 into greater conductivity. This increases the effective negative feedback to the operational amplifier 28 with an effective decreasing of the gain. The result is a flattening of the gain characteristic of the amplifier 15 to produce an essentially flattened gain curve. Applicant has found that this provides increased sensitivity to low levels of speech while still allowing a wide dynamic range. This is, of course, particularly significant where a very accurate level detection is desired for soft voice levels as well as loud voice levels.

The output of the operational amplifier 28 is connected to the first and second signal processing channels 17 and 18, which in one unique embodiment of this invention, include means for developing square wave signals for driving the feedback means wholly on and wholly off.

The adjustable level detector of the first signal processing channel 17, in the illustrated embodiment of the invention, includes an operational amplifier 33 having the non-inverting input connected to the output of the signal amplifier 15. The inverting input of the operational amplifier 33 is connected to a positive voltage source 34 through a resistor network 35 including a level setting potentiometer 36 to provide a variable reference level for operational amplifier 33.

Source 34 is a small transistor radio-type battery which, of course, supplies power to the various components as shown by the conventional positive terminal symbol +. The diode 36a in series with the positive battery terminal is to prevent accidental application of reverse polarity voltage to the components due to incorrect battery connection. The power supply connections to the several operational amplifying and other local circuit elements are conventional and therefore not shown for purposes of simplifying the illustration.

Each peak of the input voice signal 38 which appears at the non-inverting input of amplifier 33 and which is above the reference level set by the potentiometer 36 is amplified into a full scale voltage swing. It thus provides a square wave output 39 corresponding to the width of the peak signal. The square wave signal 39 is applied to a filter or averaging network 40 including a steering diode 41 connected to a paralleled resistor 42 and capacitor 43 to ground. The filter network 40 produces an essentially square wave signal 44 related to the total duration of the incoming peak signals. The square wave signal 44 will have a small unfiltered or ripple 45 component superimposed thereon. The output of the filter network 40 is applied to an inverter 46, preferably a Schmitt triggered inverter which is set to operate at a level below the peak level of the filtered square wave signal 44. The inverter not only inverts the signal 44, but removes the ripple signal portion. The output of the inverter 46 is an inverted square wave signal 47 which is fully filtered. The Schmitt trigger inverter 46, as well as the other inverters described in the preferred embodiment, is preferably an integrated CMOS Schmitt trigger providing a hystersis of approximately 45% of the supply voltage. The output is thus a very effective negative square wave signal 47. This processed signal is applied to an inverter 48 to develop a positive square voltage signal 49, which is connected directly to the loud voice contact 23 of the response selection switch 19. The output is connected to oscillator 20 for turning the oscillator 20 wholly on or off and thereby produce a positive and predetermined feedback signal.

The tone oscillator 20 is shown as a conventional oscillator including an operational amplifier 50, with suitable feedback circuits such that the output is an audible beep signal which is capacitive coupled to an output potentiometer 21 having an adjustable tap 52 coupled to the loudness control unit knob 7. The output of the tap 52 is connected directly to the earphone 3.

The inverted output 47 is also connected to the visual indicator 10 and through inverter 56 to an output terminal 53 of the jack 11 for connection to a timer 54. The illustrated visual indicator 10 includes the small LED lamp 10a connected in series with a current limiting resistor 55 to the positive voltage supply and to the output of the inverter 46. An inverter 56 also connects the inverter 46 to the loud level terminal 53 of the jack 11. Thus, whenever the voice level is above that set by the potentiometer 36, the tone oscillator 20 is actuated, the lamp 10 is lit, and a signal is applied at the timing terminal 53 as previously described.

The second channel 18 is connected to similarly detect unique voice characteristics and particularly the monitoring of essentially any voiced speech sound. The fixed level detector 24 is similar to the adjustable level detector and includes an operational amplifier 57 with a fixed reference network 58 and a noninverting input connected to the input amplifier 15. Each peak signal produces a full scale voltage swing and a square wave output signal, which is filtered at 59 and refined by a Schmitt inverter circuit 60 to produce a voice signal output at the output line of the fixed level detector. This signal is also applied to a lamp indicator 9, to timing terminal 61 and to the soft voice circuit 25, which is operative with the response switch 19 connected to the soft voice contact 26.

The soft voice circuit 25 includes a coupling diode 62 which is connected to detector 24 and to a decay timing circuit 63 including a resistor 64 in parallel with a capacitor 65 to ground 66. The timing circuit 63 has a practically instantaneous charging time and whenever significant voice signals are absent, the capacitor 65 is charged to the full supply voltage from the positive output of inverter 60. Thus full voltage is diode coupled via a diode 67 to the input of an inverter 68 which produces a relatively low output when significant voice input is absent. The inverter 68 is connected to the soft tone contact 26 and the low output of the inverter 68 maintains the tone oscillator 20 off. If the speech output is present, the inverter 60 goes low, permitting discharging of capacitor 65 through resistor 64 and producing a low input to the inverter 68 which generates a high input signal to the tone oscillator 20 tending to turn it on. In the soft tone monitor state, the channel 17 prevents such turn on if the patient is speaking sufficiently loud, as follows.

The output of the adjustable level detector 22 is also connected through a coupling diode 69 to a decay timing network or circuit 70, including a resistor 71 and a capacitor 72 to ground. A diode 73 connects the output of circuit 70 to the soft tone contact inverter 68 and to the cathode side of the coupling diode 67 from the timing circuit 63 and thus from the fixed level detector 24. If the sound level is above the threshold level set by the potentiometer 36 of detector 22, the output of the inverter 46 is low, providing a high output at the inverter 48. The capacitor 72 is thus charged, back biases diode 67 and holds the input of inverter 68 high. This, of course, holds oscillator 20 off. In this instance, the threshold level is set at a minimum level which should normally be reached unless the patient is speaking too softly. When speaking too softly, the capacitor 72 sees a low input voltage and discharges through the resistor 71. When the voltage drops below the threshold of the inverter 68, the output of the inverter 68 goes high and turns on the tone oscillator, thereby indicating to the patient that he is speaking too softly.

Thus, the dual channel circuit in addition to providing for monitoring of the abnormal time period as set by the variable threshold level and the total phonation as detected by the fixed level detector provides for continuous monitoring of the speech conditions below a selective level and providing a feedback signal indicating such condition. However, the circuit does not respond to complete voice absence to erroneously apply a feedback signal.

The relationship can be briefly summarized in the chart form as follows:

| VOICE INPUT TRANSITION | TONE OSCILLATOR |
| --- | --- |
| LEVEL 1 TO 2 | TURNS ON ONLY AFTER DELAY SET BY RESISTOR 64 AND CAPACITOR 65 |
| LEVEL 2 TO 1 | TURNS OFF IMMEDIATELY |
| LEVEL 2 TO 3 | TURNS OFF IMMEDIATELY |
| LEVEL 3 TO 2 | TURNS ON ONLY AFTER DELAY SET BY RESISTOR 71 and CAPACITOR 72 | wherein level 1 is equal to no voice input, level 2 equals a voice input which is below the threshold level of the adjustable level detector and level 3 corresponds to a voice input above such a threshold level. Level 2 is thus the abnormal condition, while levels 1 and 3 are normal conditions. The latter two levels hold the tone oscillator 20 off and only during the presence or existence of level 2 is the tone oscillator 20 turned on, and then only after a suitable delay period allowing for normal speech conditions. Thus, in particular, as shown in the chart, when the patient transition is from no speech to beginning to speak, the tone oscillator turns on only after the delay period set by the discharge time for capacitor 65 to discharge through resistor 64 to the level which turns the oscillator on. This represents a delay sufficiently long to allow for normal speech attack existing in transition from levels 1 to 3. Generally it will be approximately 0.02 seconds. When in level 2, that is speaking too softly, the patient may stop speaking and as soon as he does so, the tone oscillator 20 will instantly turn off as a result of the rapid charging of capacitor 65. If the patient, when speaking too softly, responds to the feedback signal and increases the speech level, the threshold detector 22 provides an output which immediately turns off the tone oscillator 20 as a result of charging capacitor 72 to the supply voltage. If the patient's voice again drops below the minimum level and thus transfers and moves to level 2, the output of the adjustable level detector 22 ceases and capacitor 72 discharges and, at the selected level, turns on the tone oscillator 20. The delay period from the initiation of discharge to reading the selected level is set by resistor 71 and is selected to be of a length to allow for normal speech decay and to provide for stopped consonant speech intervals associated with moving from level 3 to 1. This time is substantially longer than that of normal speech attack time and approximately 0.2 seconds. 1

The integrated circuit components of the FIG. 5 are particularly desirable in providing a very sensitive detection of the voice level permitting not only accurate level detection, but permitting the rapid turn on and off the tone oscillator to essentially eliminate the possibility of a garbled feedback sound. The tone oscillator switches rapidly on and off and can provide a relatively loud feedback sound. This is particularly desirable for training of patients who are hard of hearing or those which do not otherwise respond to a normal feedback signal. The response and feedback signal levels are readily adjusted by setting of the recessed control knobs. The three terminal jack also permits ready attachment of a timer for recording of total phonation time as well as phonation time above the threshold level, allowing complete monitoring of the voice characteristic.

The application of the device can be employed, of course, for other monitoring conditions. For example, as previously noted, a common speech problem involves speaking with a very nasal characteristics. For example as shown in FIG. 6, a microphone 75 can be applied to the side of the nose 76 of a patient to produce signals whenever a nasal emission or condition occurs during speech. The microphone 75 is preferably placed to the side of the nose immediate below the nasal bone 77 as shown in FIG. 6. If the patient in speaking uses words, sentences, or the like, with nasal emission, a feedback signal is generated. Further, although shown as a typical pressure responsive transducer any other form of microphone or other pick-up unit which can be attached to the patient and produce an output signal can be employed.

In addition, various speech conditions and the like are also associated with extreme muscle tension. Headaches and the like may be associated with abnormal muscle stresses. Other physical conditions may be associated with known body temperature conditions. An appropriate detector of such conditions can be employed to trigger a feedback signal.

Although the tone oscillator 20 provides a highly satisfactory and reliable system for most applications, it obviously cannot be employed with totally deaf patients. In such application, a signal light might be substituted. For example, a small LED lamp could be employed and attached to an eyeglass frame or other otherwise mounted adjacent to the patient's eye. In the case of a deaf and blind patient, a tactile vibrator unit might be employed as a feedback response device.

The present invention broadly provides the concept of a structure including an electronic level switching means having means to adjust the limits operated on output means. The patient may determine the particular output condition to be detected, unless, of course, the instrument is mounted to be inaccessible or such external controls are removed.

The present invention particularly provides a small compact and portable monitoring unit adapted to be worn directly by the patient for sensitive and accurate monitoring of various physical conditions and providing a direct and instantaneous feedback signal in response to abnormal conditions. The invention is uniquely and particularly adapted to speech therapy and particularly for therapeutic conditioning and care of patients with vocal intensity disorders.

Various modes of carrying out the invention are contemplated as being within the scope of the following claims, particularly pointing out and distinctly claiming the subject matter which is regarded as the invention.

We claim:

1. A portable vocal behavior treatment apparatus comprising a pick-up unit having attachment means for connection to a patient and operable to generate an output signal in response to a vocal output of the patient, an input amplifier means connected to said pick-up unit to increase the level of said signal, an automatic gain circuit connected to said input amplifier means and operable to flatten the gain curve of the amplifier means and increase sensitivity in the low sound level range without limiting response in the high sound level range, a first signal channel means having an adjustable means for detecting vocal activity of only a selected level and having an adjustable means for setting the response level to said activity, a second signal channel having means for detecting essentially all vocal activity of the patient, means connected to said first and second signal channels for monitoring the vocal activity of the patient in accordance with total vocal period and the vocal period relative to said selected level, said first and second signal channels each including a signal level detector connected to said input amplifier means and responsive to the peak level of said output signal to produce corresponding square wave detector signals in the presence of said behavior, each channel having means for summing said square wave signals to form square wave feedback signals, and inverting means connected to one channel to invert the relative potential and thereby produce an opposite logic level signal, and a logic circuit means connected to said first and second channels and producing a feedback signal only with vocal activity in the range of the second channel and below the preselected level of the first channel.

2. A portable therapeutic apparatus for providing instantaneous feedback to a patient in response to patient behavior, comprising a pick-up means for attachment to the patient and producing a behavioral signal in response to the monitored behavior, a first signal channel having a signal detector connected to said pick-up means including an adjustable level control and responsive to said behavioral signal above said selected level to produce a detector signal, signal processing means to convert said detector signal to a first constant level signal defining a first feedback signal, a second signal channel having a signal detector connected to said pick-up means and responsive to said behavioral signal to produce a second detector signal in the presence of said behavior, said second channel having signal processing means to convert said second detector signal to a second constant level signal defining a second feedback signal, said first and second constant level signals being of an opposite potential, logic circuit means connected to the first and second channels for producing a third feedback signal only in response to the combination of said second constant level signal in the absence of said first constant level signal, feedback means for generating a detectable signal to the patient, and switch means selectively connecting said first channel and said logic circuit means to said feedback means for activating said feedback means in response to said first or third feedback signals.

3. The apparatus of claim 2 wherein said logic circuit includes a steering diode network connected to said signal processing means and to an output means and producing said third feedback signal at said output means in accordance with the first and second feedback signals.

4. The apparatus of claim 3 wherein said diode network includes a first diode branch connecting the first channel to the output means, an R-C timing network connected to said branch, a second diode branch connecting the second channel to the output means, and an R-C timing network connected to said second branch.

5. The apparatus of claim 4 wherein said output means includes an inverter.

6. The apparatus of claim 4 wherein said feedback means is a tone generator.

7. The portable therapeutic apparatus of claim 2 including an input amplifier means connected to the pick-up means to increase the level of said signal, and an automatic gain circuit connected to said input amplifier means.

8. The apparatus of claim 3 wherein each of said signal detectors includes an operational amplifier having one input connected to said input amplifier and the second input connected to a reference signal, a filter circuit connected to said operational amplifier to produce a partial filtered signal, and a triggering circuit connected to said filter circuit to remove the ripple component from the filtered signal and produce said constant level signals, and an inverter circuit connected to one of said channels to invert the output of the triggering circuit.

* * * * *